United States Patent [19]

Gressel et al.

[11] Patent Number: 5,219,825

[45] Date of Patent: Jun. 15, 1993

[54] SYNERGISTIC HERBICIDAL COMPOSITIONS COMPRISING HERBICIDES WHICH GENERATE TOXIC OXYGEN RADICALS AND CHELATING AGENTS WHICH INHIBIT THEIR DETOXIFICATION

[75] Inventors: Jonathan Gressel, Rehovot; Joseph Shaaltiel, Rishon-Le-Zion, both of Israel

[73] Assignee: Yeda Research and Development Co., Ltd., Rehovot, Israel

[21] Appl. No.: 100,319

[22] PCT Filed: Feb. 3, 1987

[86] PCT No.: PCT/US87/00221

§ 371 Date: Nov. 9, 1987

§ 102(e) Date: Nov. 9, 1987

[87] PCT Pub. No.: WO87/04596

PCT Pub. Date: Aug. 13, 1987

[30] Foreign Application Priority Data

Feb. 6, 1986 [IL] Israel ........................................ 77817

[51] Int. Cl.⁵ .................... A01N 43/40; A01N 43/70; A01N 47/14; A01N 63/00

[52] U.S. Cl. .................................. 504/117; 504/118; 504/127; 504/130; 504/133; 504/134; 504/135; 504/136; 504/143; 504/144; 504/148

[58] Field of Search .................... 71/101, 94; 504/117, 504/118, 127, 130, 133, 134, 135, 136, 143, 144, 148

[56] References Cited

U.S. PATENT DOCUMENTS

2,992,091 7/1961 Harman et al. .................... 71/101

OTHER PUBLICATIONS

Klingman et al., "Weed Science Principles and Practice", pp. 165–168, John Wiley & Sons, 2nd edition, 1982.

Sawada et al., Biochim. Biophys. Acta 268, 305, 1972.

Heikkila et al., "The inactivation of copper zinc superoxide . . . " Chemical Abstracts, vol. 89, pp. 177, 72412W, 1978.

Muneta. Chem. Abst. vol. 94, (1981) 155220M.

Burdeska et al. Chem. Abst. vol. 97 158036d, also pp. 1625H, 11th collectives Index.

*Primary Examiner*—Glennon H. Hollrah
*Assistant Examiner*—S. Mark Clardy
*Attorney, Agent, or Firm*—Browdy and Neimark

[57] ABSTRACT

The invention relates to synergistic herbicidally active compositions. The quantity required for a given herbicidal effect is substantially lower than that required for the herbicide itself. The compositions of the invention comprise in combination a herbicide which brings about active oxygen species formation in plants and a substance which binds copper or zinc, or a substance which reacts with a thiol moiety of a thiol containing enzyme. The herbicide and metal binding or thiol binding component can be applied together or separately.

13 Claims, No Drawings

SYNERGISTIC HERBICIDAL COMPOSITIONS COMPRISING HERBICIDES WHICH GENERATE TOXIC OXYGEN RADICALS AND CHELATING AGENTS WHICH INHIBIT THEIR DETOXIFICATION

FIELD OF THE INVENTION

The invention relates to improved herbicidally active compositions. These are based on the discovery that when a herbicide which generates an active oxygen species, when applied to plants, is used together with either a substance suited to bind metal or thiol groups in enzymes which participate in the detoxification of active oxygen species containing such metals or thiol groups which are present in the weeds, these enzymes are inhibited. The added substance binds the specific metals present in such enzymes or the thiol groups in said enzymes and cause them to lose activity. The metals most commonly present are copper and zinc. The inactivation of the active oxygen species generated by the herbicide is thus substantially reduced by a factor of more than five allowing much less herbicide to be used for a given effect.

BACKGROUND OF THE INVENTION

There exist large variations in the effective dose of oxidant-producing herbicides (i.e., herbicides that bring about formation of active oxygen species required to kill plants). With bipyridillium herbicides such as paraquat, (1,1'-dimethyl-4-4'bipyridium ion) there exists a considerable variation in susceptibility among weed species. Some species, such as *Bromis inermis, Amaranthus retroflexus* and wheat, are killed at 0.01 kg/ha, whereas, at the other extreme, 3 kg/ha (i.e., 300 times more) are required for good control of Digitaria. *Chenopodium album, Sinapis arvensis* and *Galium aparine* under standard industrial screening conditions (Mr. Pierre Bocion, Dr. R. Maaq Ltd., Dielsdorf, Switzerland, personal communication). Biotypes of certain weed species have evolved resistance to paraquat and are not killed by 16 kg/ha while the sensitive biotype of the same species is controlled by 1kg/ha (Watanabe et al., Weed Research (Japan) 7 49, (1982)). In plants a system is known which detoxifies superoxide normally produced as a dangerous byproduct of photosynthesis. (Scheme 1).

ferrous ions to highly toxic hydroxyl ions by the Fenton reaction. This multiple enzyme system exists in varying levels in different plant species and biotypes. The first enzyme in this sequence (superoxide dismutase) has been reported to be in higher activity levels in tissues of biotypes of species with higher levels of tolerance to paraquat. (Harvey and Harper in Le Baron and Gressel, "Herbicide Resistance in Plants, Wiley p. 215 (1982); Youngman and Dodge, Proc. 5th Intl. Photosyn. Con. Balahan Intl. Sci., Philadelphia p. 537 (1981); Furusawa et al., Plant Cell Physiol. 25 1247 (1984). These findings have been debated as others, including ourselves, (Fuerst et al., Plant Physiol. 77 984 (1985); Shaaltiel and Gressel, Pestic. Biochem. Physiol. 26 22, (1986), could not repeat their results using the methods stated. Superoxide dismutase is also found in higher activity levels in plants chemically stimulated to higher levels of tolerance to paraquat, an oxidant-generating herbicide (Lewinsohn and Gressel, Plant Physiol. 76 125 (1984)). Plants with a ratio of the antioxidants; ascorbate to alpha-tocopherol of more than 5 and less than 20 were far more tolerant to the photo-oxidant affect of the diphenyl-ether herbicide oxyfluorfen [2-chloro-1(3-ethoxy-4-nitrophenoxy)-4-trifluoromethyl)-benzene] (Finckh and Kunert, J. Agric. Food Chem. 33 574 (1985)). Thus ascorbate regenerated by the system can be active in quenching toxic singlet oxygen produced in the presence of some oxidant generating herbicides.

Plants containing higher or lower ratios were more susceptible. Of the enzymes described, it is known that superoxide dismutase contains both copper and zinc (Sawada et al., Biochim. Biophys. Acta 268 305 (1972)). Ascorbate peroxidase, which competes with the Fenton reaction for the peroxide, contains copper and iron (Asada et al., in "Oxidative Damage and Related Enzymes, Harwood Acad. Press p. 342 (1984)). Glutathione reductase and dehydroascorbate reductase are both thiol containing enzymes (Hossain and Asada, Plant Cell Physiol. 25 85 (1984); Halliwell and Foyer, Planta 139 9, (1978)).

SUMMARY OF THE INVENTION

There are provided synergistic herbicidal compositions which contain a combination of an active oxygen-species producing herbicide and an agent which complexes or chelates metal ions of metal-ion containing plant enzymes and/or bind or complex thiol groups of Scheme 1:

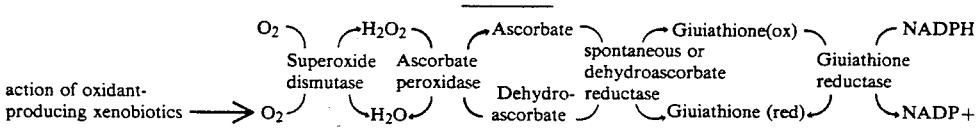

The superoxide dismutating system in plants Such oxygen radicals are naturally produced in low amounts as products of photosynthesis especially at high light intensities (Fover and Halliwell, Planta 133 21 (1976); Nakano and Asada, Plant Cell Physiol. 22 867 (1981); Asada et al., in "Oxidative Damage and Related Enzymes" Harwood Acad. Press, London p.342 (1984)). It has been proposed that superoxide-dismutase converts the oxygen radicals to hydrogen peroxide (which is also toxic) and this in turn is detoxified in a series of steps with ascorbate peroxidase, glutathione reductase and-/or dehydroascorbate reductases. Conversely, the peroxide can be chemically converted in the presence of thiol-group containing enzymes of plants. The enzymes referred to are those which take part in the superoxide detoxification pathway of plants and which also provide glutathione and ascorbate which quench singlet oxygen. The patent and scientific literature is replete with herbicidally synergistic compositions. These include two types of synergisms which are unrelated to the synergism that is the the subject of this patent application. The first type of known synergism is where a mixture of two known herbicides interact synergistically to provide greater kill of a given weed species or a broader spectrum of herbicidal activity (more weed species killed at synergistic rates of application). Examples of this type of synergism are described in U.S. Pat. Nos. 4,517,009 (Slife), 4,378,990 (Schering) 4,358,308 and 4,473,392 (Wuerzer). The second type of synergism described is where an adjuvant prevents the degradation of a herbicide by plants, extending the effectual life of the herbicide, providing sufficient time for phytotoxicity to be manifested, and requiring less herbicide because of the lower rate of degradation. Such compounds can be inhibitors of mixed function oxidases (cf. Gaillardon et al., Weed Res. 25 297 (1985)), aryl-acyl amidases (cf. Lamoureux and Rusness, Pestic. Biochem. Physiol. 26 323, (1986)) or compounds which inhibit glutathione-S-transferases (Lamoureux and Rusness op. cit). Tridiphane is an example of a compound which has some herbicidal activity alone on grasses and is synergistic with the herbicide atrazine because it prevents the degradation of atrazine (Lamoureux and Rusness op. cit and U.S. Pat. No. 4,110,104).

The present invention is based on a principle different from the above: it is based on enhancing effective herbicide activity by preventing the degradation of some of the phytotoxically active oxygen species produced by the interaction of herbicide and plant. These oxidants are the phytotoxically active species and, when detoxified, the plant does not die, unless higher rates of herbicide application are used.

It has been discovered that certain metal-containing enzymes and thiol-group containing enzymes hamper the phytotoxic activity of active oxygen-species producing herbicides, when such enzymes are present in the weeds. The amount of herbicide required for phytotoxicity is a function of the amounts of these enzymes and their products.

The present invention is based on the discovery that such enzymes can be inactivated by complexing or chelating agents or chemical compounds which interact with the metal cations of such enzymes and/or with the thiol groups of thiol-containing enzymes. The agents that interact with the metal cations and/or the thiol groups can be combined with the herbicide in one composition; there can also be provided separate compositions which are applied one after the other or which can be applied simultaneously. The combined effect is a synergistic one, and the effect of the herbicides of this type is greatly enhanced, especially when used with weeds which have a certain resistance to members of this type of herbicide. The concept of the invention is especially applicable with herbicides which interact with the photosynthetic or respiratory electron-transport chains in plants resulting in the production of active oxygen species. Amongst suitable herbicides there may be mentioned those of the triazine, phenylurea, nitro-diphenyl ether, uracil and bipyridillium class. This list is not an exhaustive one, and it is clear that the invention is applicable to herbicides whose effect is at least partially counteracted by the presence of high concentrations of enzymes of the type set out above. Amongst cations present in this type of enzymes there may be mentioned cations of copper, zinc, manganese and iron. Some of the complexing or chelating agents may have by themselves a certain herbicidal effect, but this is negligible in comparison with the synergistic effect of the combination of the herbicides producing active oxygen species and metal-cation and/or thiol-group containing enzyme inactivating agents. The compositions of the invention (be it a combination or a simultaneous or separate application of the two ingredients) deplete the weeds to a certain extent of their capability to detoxify active oxygen species, and thus the threshold of the levels of herbicide required to result in the desired control of such weeds is considerably decreased and substantially lower quantities of herbicide need to be applied for a given effect. There may be used a wide variety of agents suited to bind the thiol groups of the thiol-containing enzymes: amongst these there may be mentioned N-ethylmaleimide, iodoacetate, chloro-mercuribenzoate, but these have a comparatively high degree of toxicity to mammals and man and thus in agriculture their use will be restricted to those applications only where such toxicity is not harmful. It is possible to resort to the use of other chemicals which will provide the desired thiol-binding effect and which are of lower toxicity. As regards metal-cation binding agents (complexing, chelating agents) there are used mainly those which interact with the main cations found in the metal-containing plant enzymes which take part in the pathway of detoxification of active oxygen species, namely manganese, copper, iron, and zinc. There exists a wide variety of suitable, comparatively non-toxic agents suitable for this purpose. Amongst these there may be mentioned diethyldithio-carbamate; $\alpha, \alpha'$-dipyridyl; ethylene diamine tetraacetic acid; tetraethylene pentamine; ethylene-diamine; ethylene triamine; triethylamine tetraamine, 8-hydroxyquinoline, diethyl-dithiocarbamate, salicyl aldoxime, iron-binding hydroxamic acids, p-hydroxy pyridine, etc. Those of these chelators that bind iron preferentially to copper and zinc may not be active as they deplete the iron from the organism, preventing the Fenton reaction which converts moderately toxic peroxide to highly toxic hydroxyl ions. As stated above, there may be used compositions which contain the herbicide together with the metal-binding compound and/or with the thiol-group binding compound; or there may be used as separate compositions of the herbicide and of one or both of the others, to be applied simultaneously or one after the other. The results obtained hitherto demonstrate that the synergistic compositions of the invention lead to a decrease in the quantity of active oxygen producing herbicides by a factor of about 5 to 30 calculated on the quantity of such herbicide used by itself to obtain an identical effect.

Various plant pathogenic micro-organisms, especially fungi, are used as "bio-herbicides" or mycoherbicides. Their use is limited because of inordinately high inoculum levels that must be sprayed to obtain control of noxious plants. This is due, in some cases, to the active oxygen detoxifying defensive systems within the plants. Some mycoherbicidal fungi kill plants by secreting photodynamic agents which are absorbed by the plants. These compounds then cause the generation of active oxygen species with the same result as that obtained with oxidant generating herbicides (cf. Knox and Dodge, Photochem. Photobiol. 24 889, (1985)). The high inoculum levels are needed to overcome the active oxygen degrading system of the plant. The synergists of this invention, added with the inoculum of such myco- or bio-herbicides, can suppress this natural defense system, vastly lowering the level of required inoculum.

The synergistic compositions of the present invention are useful in lowering the quantity of herbicide needed in agronomic situations. One major exception may be when the oxidant-generating herbicide is being used as a selective phytotoxicant, i.e., to kill weeds within a crop. If crop tolerance to such herbicide is due to high levels of the oxidant detoxification pathways, then a synergist can cause phytotoxicity to such crops.

A major use of the novel compositions is in no-till agriculture; i.e., where crop, pasture or sod are planted without plowing or disc cultivation of the field. Paraquat is a widely used herbicide for this purpose as it kills only those plants that it contacts, and becomes herbicidally inactive upon reaching the soil. The compositions can lower the dose and thus the cost of this herbicide which has higher mammalian toxicity than most herbicides. Some herbicide selectivities are due to crop degradation of the herbicide, and there are cases of marginal selectivity where the crop degrades the herbicide too slowly. By lowering the dose of herbicide, due to the presence of a synergist, such crop can now be rendered sufficiently tolerant to the herbicide to allow its use as a selective herbicide.

Some of the herbicides (e.g. paraquat) have been used as dessicating agents to aid the harvest of crops; i.e. to dry leaves before harvest to facilitate mechanical harvest. Such crops include cotton, soya, potatoes and many of others. This use is highly amenable to synergistic compositions of the invention.

The oxidant generating herbicides depend, in most agronomic situations, on sunlight as the energy source to generate active oxygen species. On cloudy or partly cloudy days they are far less active, and the herbicides are often dissipated from the plant before toxicity is attained. Synergistic compositions of the invention lower the amount of light required to create sufficient active oxygen species for herbicidal effect. With herbicidal compositions of the invention there exist fewer problems of herbicide leaching into ground water as well as herbicide phytotoxic carryover from season to season as less herbicide is used.

The following examples illustrate that:

(i) the differences in oxidant herbicide levels needed to control plants are correlated with differences in organella levels of the enzymes of the pathway of degradation of active oxygen species;

(ii) that these enzymes are inhibited by compounds which complex metals and by compounds that complex thiol groups;

(iii) that the same compounds act as synergists for oxidant-producing herbicides when applied with said herbicides on plant parts (in vitro systems) and when applied to whole plants.

EXAMPLE 1

This demonstrates that elevated levels of enzymes of the pathway for detoxifying active oxygen species are present in plant material requiring a higher level of the oxidant producing herbicides to obtain phytotoxicity Seeds of two biotypes of *Conyza bonariensis* (L.) Cronq. (synonym *C. linifolia*) were obtained from Egypt. The paraquat sensitive biotype was gathered near Alexendria and seeds of the resistant type from the Tahrir irrigation district. They were obtained from Dr. Martin Parham in England. Seeds were germinated in a growth room with a 14 h light period at 25° C. Plants were transferred out of doors 24 h before being sprayed. The phytotoxicity of three herbicides representative of the three different modes of generating active oxygen species known at present. Commercial paraquat (Gramoxone-ICI Plant Protection Ltd) was formulated with 0.1% (w/v) Tween-20 (a non-ionic surfactant) for spraying. The response to the range of $10^{-5}$M to $10^{-2}$M paraquat was measured by spraying two plants per concentration to run-off in the early morning. All plants were exposed to sunlight for at least 13 h (1300 $\mu E.m^{-2}s^{-1}$ photosynthetically active radiation (PAR) at mid day). Commercial acifluorfen (Blazer, Rohm, and Hass, Philadelphia, Pa., USA) to which was added 0.25% Tween-20 was sprayed to run-off. The response to spraying was measured as with paraquat 24 h after spraying. Commercial atrazine (Atranex 50 WP-Agan) was sprayed at various rates in 0.25% Tween 20 to run off. Fully expanded, 8 to 10 cm long leaves from plants in the rosette stage were used in all experiments. Phytotoxicity of acifluorfen and paraquat was measured as $CO_2$ fixation 24 h later as follows: Detached leaves were placed on wet filter paper in a sealed chamber with $5\mu$ $Ci^{14}C$-sodium bicarbonate. Tartaric acid was remotely dripped on the sodium bicarbonate to release $^{14}CO_2$. Leaves were illuminated with 148 $\mu E.m^{-2}s^{-2}$ (PAR) for 30 min. Eighty percent acetone was added and the mixture put under strong light to photobleach pigments and evaporate the acetone. A scintillation mixture of Lumax:xylene (45:55) was added to the leaves and remaining water. The samples were counted and the data expressed as $DPM.cm^{-2}$. Area was measured with a planimeter from photocopies of the leaves made prior to photosynthesis measurements. Phytotoxicity of atrazine was measured as the elevated level of malonyldialdehyde in the tissue. Malonyldialdehyde (as measured with thiobarbituric acid according to Dodge and Gillham (Asp. Appl. Biol 11 97 (1986)) is a measurement of lipoxidation of unsaturated fatty acids, and provides an excellent estimation of damage by active oxygen species.

$CO_2$ assimilation ceased in the resistant biotype at $10^{-3}$M paraquat and in the wild biotype at $10^{-5}$M paraquat (Table I). The same two biotypes were treated with the nitro-diphenylether herbicide acifluorfen. There are different views on how this herbicide group acts to generate active oxygen species in the light. It clearly acts elsewhere than paraquat or atrazine. It is clear that the plant material that evolved resistance to paraquat also has some tolerance to acifluorfen, another oxidant producing herbicide as well as to atrazine (Table I).

TABLE 1

Differences in phytotoxicity of different *Conyza bonariensis* biotypes to oxidant producing herbicides

| Herbicide | molar conc. | paraquat sensitive biotype | paraquat tolerant biotype |
|---|---|---|---|
| | | % photosynthesis inhibition | |
| control | 0 | 0 | 0 |
| paraquat | $10^{-5}$ | 95 | 0 |
| | $3.2 \times 10^{-5}$ | 100 | 0 |
| | $10^{-4}$ | 100 | 0 |
| | $3 \times 10^{-4}$ | 100 | 48 |
| | $10^{-3}$ | 100 | 97 |
| | $3 \times 10^{-3}$ | — | 100 |
| acifluorfen | $10^{-4}$ | 23 | $0^a$ |
| | $3.2 \times 10^{-4}$ | 40 | $0^a$ |
| | $10^{-3}$ | 58 | 21 |
| | $3.2 \times 10^{-3}$ | 72 | 67 |
| | $10^{-2}$ | 98 | 99 |
| | | malonyldialdehyde in tissue (% untreated control) | |
| atrazine | $1.0 \times 10^{-2}$ | 100 | 100 |
| | 1.5 | 135 | 100 |
| | 2.0 | 130 | 100 |
| | 3.0 | 155 | 100 |
| | 4.0 | 225 | 100 |

TABLE 1-continued

Differences in phytotoxicity of different *Conyza bonariensis* biotypes to oxidant producing herbicides

| Herbicide | molar conc. | paraquat sensitive biotype | paraquat tolerant biotype |
|---|---|---|---|
| | 5.0 | 320 | 125 |

[a]There was actually some stimulation (hormesis) at this concentration.

Based on preliminary evidence that there was no difference in superoxides dismutase activity in whole leaves of these two biotypes and our own findings we assayed the levels of the dismutating enzymes in chloroplast extracts. The oxidant producing herbicides are effective in field conditions only in the light. The superoxide radical and the hydrogen peroxide produced in the first steps of dismutation do not leave the intact plastid and first disrupt its membranes. This justifies assay of these enzymes in chloroplasts. Intact chloroplasts were isolated according to the method of Slovacek and Hind (Plant Physio. 60, 538 (1977)) except that 50 mM 2-(N-morpholino)ethanesulfonic acid buffer was used instead of the pyrophosphate buffer originally used in the chloroplast isolation medium. The chloroplasts were resuspended in 2 ml of 0.36M sorbitol brought to pH 7.5 with solid tris-(hydroxymethyl)amino-methane as per Nakatani and Barber (Biochim. Biophys. Acta 461 510 (1977)) and centrifuged at 2400×g for 10 sec. The pellet was suspended in the same sorbitol-tris(hydroxymethyl)-aminomethane buffer. The chloroplasts were used for enzyme measurements immediately after isolation. Chlorophyll content was measured in 80% acetone according to Arnon (Plant Physiol. 24 1 (1948)). Intactness of chloroplast was measured by means of ribulose-bis-phosphate-carboxylase activity in the chloroplast fraction supernatant according to Bjorkman (Physiol. Plant 21 1, (1968)), and proteins by the method of Bradford (Analyt. Biochem. 72 248 (1976)). The chloroplasts were burst to allow assay of enzymes in a French pressure cell. Superoxide dismutase was assayed on extracts of the chloroplants by separating proteins on 10% polyacrylamide gels by the method of Laemmli (Nature 227 680 (1970)) but without sodium dodecyl sulfate on 2 mm thick and 20 cm long gels. The gels were run at a constant voltage of 120 mV for 14 h and stained for superoxide dismutase activity with nitro blue tetrazolium in the presence of riboflavin and illuminated for 30 min according to Beauchamp and Fridovich, (Analyt, Biochem. 44 276 (1971)). Nitrol-blue tetrazolium turned from light-yellow to dark-blue upon reduction by superoxide produced by riboflavin in the light. Nitro-blue tetrazolium was not reduced in the band with superoxide dismutase and the gel three remained transparent. We developed a technique to quantify superoxide dismutase by generating a standard curve by running different levels of known superoxide dismutase (ex bovine blood, Sigma) on the same gel. Superoxide dismutase units were defined as per McCord and Fridovich (J. Biol. Chem. 244 6049 (1969)). The gels were scanned in a Beckman DU-8 spectrophotometer, the peak areas were measured and related to the superoxide dismutase standard curve which was linear up to 0.2 enzyme units. The actual amounts of chloroplast superoxide dismutase were also measured immunochemically using an antibody prepared against the chloroplast isozyme prepared from oats.

Glutathione reductase activity was spectrophotometrically measured in chloroplast extracts by following the decrease in absorption at 340 nm due to oxidation of NADPH by glutathione according to Foyer and Halliwell (Planta 133 21 (1976)). The actual amounts of this enzyme were also measured immunochemically using an antibody prepared against this enzyme form spinach.

Ascorbate peroxidase activity was measured by following oxidation of ascorbate to dehydroascorbate in a spectrophotometer at 290 nm according to Nakano and Asada (Plant Cell Physiol. 22 867 (1981)). No change in adsorption was seen in the absence of ascorbate in the medium. The results of the enzyme assays are summarized in Table II.

TABLE II

Increase in dismutating enzyme activity levels in chloroplasts of biotypes of *Conyza bonariensis* requiring different levels of oxidant-producing herbicides for phytotoxicity.

| | activity level in biotype requiring | | |
|---|---|---|---|
| | low levels of oxidant herbicide | high levels of oxident herbicide | |
| Enzyme | units per mg protein | | ratio[a] |
| Superoxide dismutase | 1.04 | 1.67 | 1.60 |
| Ascorbate peroxidase | 0.74 | 1.85 | 2.50 |
| Glutathione reductase | 0.64 | 1.87 | 2.92 |

[a]Similar ratios between the actual levels of superoxide dismutase and glutathione reductase in the two biotypes were also found when the enzyme protein was measured immunochemically.

EXAMPLE 2

This examples illustrates the inhibition of enzymes having elevated activity in plants requiring more oxidant-producing herbicide for phytotoxicity Chloroplasts were prepared and enzyme activities were measured as described in Example 1. From the data in Table III it is clear that the activity of the plastid superoxide-dismutase, including the elevated component is inhibited by a compound known to interact with such enzymes. The gel used to purify superoxide dismutase was soaked with (or without) 0.2% diethyldithiocarbamate prior to measuring enzyme activity as in Example 1.

TABLE III

Inhibition of activity of superoxide dismutase extracted from chloroplasts of *Conyza bonariensis* requiring varying levels of oxidant producing herbicides for phytotoxicity.

| | % inhibition of activity in biotypes requiring | |
|---|---|---|
| | low levels of oxidant herbicide | high levels of oxidant herbicide |
| control | 0 | 0 |
| 0.2% of sodium diethyl-dithio carbamate | 100 | 100 |

EXAMPLE 3

This example demonstrates of synergism by a metal chelator using isolated cells

Isolated cells offer an excellent rapid method of screening for phytotoxicity using a large number of potential chelators and synergists. *Asparagus sprengeri* cells were isolated from cladophylls of field grown plants using the procedure of Colman et al. (Can. J. Botany 57 1505, (1979)) except that the isolation, washing and culture buffer was 50 mM HEPES brought to pH 7.2 with KOH. The cladophylls were surface sterilized using 80% aqueous ethanol. After three centrifugations to remove broken cells, the cells were diluted to 10% packed volume and 0.75 ml were placed in each well of cluster dishes. The potential synergists in this example 0.02% w/v final concentration diethyldithiocarbamate (DDC) and an oxime of 4-octyl-2-acetylphenol (U.S. Pat. No. 4,215,219) which complex primarily with copper and di-2-ethylhexyl-phosphoric acid which complexes primarily with zinc (Flett, Chem and Ind. 17 706, (1977)) was placed with the herbicides atrazine and paraquat. All additions were made at 100 fold the final concentration of herbicide and synergist. Paraquat was dissolved in water and atrazine in methanol. The cluster dishes were incubated on a reciprocal shaker with a clear plastic bottom and illuminated from top and bottom with fluorescent lights emitting 135 $\mu Ein.m^{-2}s^{-1}$ (top) and 170 $\mu Ein.m^{-2}s^{-1}$ (bottom). The cells were kept mixed by the shaker and incubation was at room temperature. Incubation was stopped when there was visually obvious loss of chlorophyll due to treatments in a given experiment. The cells were removed to glass centrifugation tubes, centrifuged and the supernatant removed. One ml of 80% aqueous acetone was added to extract chlorophyll, the debris were sedimented by centrifugation and chlorophyll was spectrophotometrically determined at 645 and 663 nm according to Arnon (Plant Physiology 24 1, (1949)). The results (Table IVa) clearly show that concentrations of paraquat and atrazine which were ineffectual, were effectual when DDC was added at a concentration that itself was ineffectual. In another experiment, a larger variety of chelating synergists and oxidant generating herbicides were used, and light was given at a much higher intensity 1000 $\mu Ein\ m^{-2}s^{-1}$ to better approach natural sunlight which is at 1200–1500 $\mu Ein\text{-}s^{-1}\text{-}cm^{-2}$. The results are summarized in Table IVb.

TABLE IVa

Synergism of herbicides by a chelator at the cellular level using isolated *Asparagus sprengeri* cells at low light intenities (305 $\mu Ein\ m^{-2}\ s^{-1}$)

| Concentration of DDC (%) | Concentration of herbicide | | | |
|---|---|---|---|---|
| | None | $10^{-6}$ Paraquat | None Atrazine | $3 \times 10^{-6}$M ... $10^{-5}$ |
| | | % of control chlorophyll | | |
| 0 | 100 | 107 | 100 | 95   92 |
| 0.02 | 116 | 11 | 120 | 40    8 |

Paraquat toxicity was measured 24 h after treatment and atrazine toxicity was measured 40 h after treatment.

TABLE IVb

Synergism of herbicides of copper and zinc chelators at the cellular level using isolated *Asparagus sprengeri* cells at higher light intensities (1000 $\mu Ein \cdot m^{-2}\ s^{-1}$)

| Chelator | chelator concentration (%) | Concentration herbicide paraquat ($\mu$M) | | |
|---|---|---|---|---|
| | | 0 | 10 | 20 |
| | | chlorophyll remaining - % of control | | |
| Pyridine-2,6-dicarboxylic acid | 0 (herbicide only) | 100 | | 9 |
| | 0.005 | 100 | | 15.3 |
| di-2-ethyl-hexyl-phosphoric acid | 0 (herbicide only) | 100 | | 72 |
| | 0.001 | 98 | | 19 |
| Tetraethylene-pentamine | 0 (herbicide only) | 100 | 89 | |
| | 0.025 | 99 | 19 | |
| 4-Octyl-2-acetyl-phenol oxime | 0 (herbicide only) | 100 | | 74 |
| | 0.125 | 96 | | 3 |
| Triethylene-tetramine | 0 (herbicide only) | 100 | | 56 |
| | 0.008 | 90 | | 22 |

Paraquat toxicity was measured 14 h after treatment.

EXAMPLE 4

Effectivity of metal chelators as syngerists in leaves

Seeds of *Conyza bonariensis* were germinated and plants cultivated as outlined in Example 1. Other species were germinated in a similar mixture and treated at 10 days.

Sodium diethyldithiocarbamate (DDC) and the oxime of 4-octyl-2-acetylphenol were used as examples of chelators with a partial specificity for copper but will chelate other metals. Di-2-ethyl-hexyl phosphoric acid was used as a chelator with a preference towards zinc, but will also chelate other metals.

The commercial fungicides, maneb [manganese ethylene-bis(dithiocarbamate) (polymeric)] and zineb [zinc ethylene-bis (dithiocarbamate) (polymeric)] were used, they have similar structures and effects as DDC, but are blocked and act as chelate controls they have similar structures and effects as DDC but are to clarify that a synergism would be due to the chelating effect of diethyldithiocarbamate. Neither maneb nor zineb had synergistic effects with paraquat, the model oxidant producing herbicide used. They could not chelate copper due to their being blocked. The paraquat resistant biotype of *Conyza bonariensis* is hardly affected by a 1 mM spray of paraquat and much less paraquat required when DDC was added (Table V). Thirty-fold less paraquat was needed to kill the sensitive biotype of *C. bonariensis* when DDC was added (Table V).

TABLE V

Synergism of paraquat by sodium diethydithio-carbamate (DDC) in whole plants of various species.

| | Paraquat concentration ($\mu$M spray, to run-off) | | | | | | |
|---|---|---|---|---|---|---|---|
| | 0 | 1 | 10 | 30 | 100 | 300 | 1000 |
| | visual rating[a] | | | | | | |
| *Conyza bonariensis:* low herbicide requiring biotype control (herbicide alone) | 0 | 0 | 0 | 1.8 | 3 | 3 | 3 |
| +0.75% DDC | 1 | 2 | 2 | 2.0 | 1.6 | 2.8 | 3 |
| High herbicide requiring biotype control (herbicide alone) | 0 | 0 | 0 | 0 | 0 | 0 | 0.9 |
| +0.75% DDC | 0 | 0.8 | 0 | 0.6 | 0.5 | 2.4 | 2.7 |
| Beans control (herbicide alone) | 0 | 0 | 1 | 1 | 1.5 | 2 | 3 |
| +0.75% DDC | 0 | 1 | 1.5 | 1.5 | 2 | 3 | 3 |
| *Galium aparine* control (herbicide alone) | 0 | | 0 | | | | |
| +0.75% DDC | | | 1.5 | | | | |
| *Sinapsis arvense* control | 0 | | 0.5 | | | | |
| (herbicide alone | | | | | | | |
| +0.75% DDC | 0 | | 2.5 | | | | |
| *Stellaria media* control | 0 | | 0.5 | | | | |
| (herbicide alone) | | | | | | | |
| +0.75% DDC | 0 | | 3.0 | | | | |

% DDC is W/V
[a]visual ratings (scored 1 day after treatment): 0 - no damage to slight burn; 1 - moderate burn (may regenerate); 2 - severe burn (will die); 3 - death

TABLE VI

Synergism of atrazine by sodium diethyldithiocarbamate (DDC) using Conyza bonariensis biotypes requiring low and high amounts of oxidant generating herbicides for phytotoxicity.

| | Atrazine concentration (μM spray to run off) | | | | | |
|---|---|---|---|---|---|---|
| | visual ratings[a] | | | membrane damage[b] | | |
| | 0 | 15 | 30 | 0 | 20 | 40 |
| Visual ratings[a] | | | | | | |
| Low herbicide requiring biotype | | | | | | |
| control | 0.5 | 2.1 | 2.3 | 100 | 130 | 225 |
| to 05.% DDC | 1.6 | 2.7 | 2.8 | 125 | 230 | 320 |
| High herbicide requiring biotype | | | | | | |
| control | 0 | 1.7 | 1.7 | 100 | 100 | 100 |
| to 0.5% DDC | 0.6 | 2.3 | 1.8 | 112 | 215 | 263 |

[a]Visual ratings scored one day after treatment as in Table V
[b]membrane damage was measured as malonyldialdehyde release
a & b are from separate experiments Similarly, both the paraquat resistant and sensitive biotypes of Conyza bonariensis were treated with two other oxidant generating herbicides. Atrazine (of the triazine group) is the most widely used oxidant generating herbicides in agriculture. We used various dilutions of a commercial wettable powder (Atranex 50WP-Agan Chemicals) to which we added 0.5% DDC. The effects were scored 24 h later. From the data (Table VI) it is apparent: (a) that more atrazine was required to affect the paraquat resistant biotype and (b) that DDC synergized the effect of atrazine. We also tested to see whether acifluorfen, a nitro diphenyl ether herbicide would be synergized. It is generally agreed that light and oxygen are required for its action via oxidant damage. We sprayed a commercial formulation of acifluorfen (Blazer, Rohm and Haas) to which were added 0.25% Tween-20 detergent, with and without DDC. The effects were scored 24 h later. From the data (Table VII) it is apparent that (a) more acifluorfen was required to affect the paraquat resistant biotype and (b) that DDC synergized the effect of acifluorfen.

In experiments with bean leaf discs floated on a mixture of the herbicide paraquat and/or synergist in water, the dose of paraquat required to 50% inhibit photosynthetic activity was shifted to a tenfold lower dose with 0.75% diethyldithiocarbamate. These experiments show that a metal chelator is effective in synergizing paraquat and other herbicides causing formation of active oxygen species at the whole plant level. We used this bean leaf disc system to ascertain the potential of chelators to synergize a large variety of phytotoxicants purported to act by generating active oxygen species in the light. The results are summarized in Table VIII.

TABLE VII

Synergism of acifluorfen action by sodium diethydithiocarbamate using Conyza bonariensis biotypes requiring low and high amounts of oxidant generating herbicides for phytotoxicity.

| | Acifluorfen concentration (μM spray to runoff) | | | | | |
|---|---|---|---|---|---|---|
| | 0 | 30 | 100 | 0 | 3 | 100 |
| | visual rating[a] | | | photosynthesis[b] | | |
| low herbicide requiring biotype | | | | | | |
| control (acifluorifen only) | 0 | 2 | 3 | 100 | 75 | 10 |
| acifluorfen + 0.5% DDC | 0 | 3 | 3 | 92 | 0.4 | 0.3 |
| high herbicide requiring biotype | | | | | | |
| control (acifluorifen only) | 0 | 1 | 2.5 | | | |
| acifluorfen + 0.5% DDC | 0 | 2.5 | 3.0 | | | |

[a]Visually scored as per Table V 24 h after treatment
[b]photosynthesis ($^{14}CO_2$ fixation) was used as an additional measurement of phytotoxicity. Leaf discs were removed 5 h after treatment for measurement
a & b are from different experiments.

TABLE VIII

Synergizing herbicides with di-2-ethyl-hexyl phosphoric acid, a putative zinc chelator, measured using a bean leaf disc bleaching assay

| | herbicide concentration (μM) | | | |
|---|---|---|---|---|
| | acifluorfen | | paraquat | |
| Chelator concentration (% w/v) | 0 | 3 | 0 | 20 |
| | (chlorophyll - % of control) | | | |
| 0 (herbicide only) | 100 | 91 | 100 | 52 |
| 0.01 | 98 | 49 | 98 | 11 |
| 0.02 | 91 | 23 | | |

Bean discs were incubated on solutions containing the above mixtures for 5 h at 450 $\mu Ein.m^{-2}s^{-1}$ and the chlorophyll remaining in the leaves was assayed.

The compositions of this invention are also useful for sod (turf, alfalfa, pasture, etc.) renovation or conversion procedures. Thus, for example, in situations where a sod or parts thereof has become overgrown with undesirable plant species, the plants in said area can be sprayed with a mixture of herbicide and synergist of this invention to control all growing plants and from about 2 to 48 hours later depending on weather conditions, the desired species can be seeded into the dying vegetation. Where a seed bed is to be prepared only the same time need elapse (if paraquat or other herbicide with similar properties is the herbicide used) between treatment and seed bed preparation, in order to provide sufficient time for the composition to act on the undesired plants. With other more residual herbicides (e.g. phenyl-ureas and triazines) a much longer period may be required due to soil persistence. In an alternate method of sod renovation, the area can be seeded and immediately sprayed with a mixture of synergist and a compatible herbicide lacking residual activity as per this invention. In either method, the seeds fall among the vegetation as the sprayed plants wither and die, they act as a mulch and moisture retaining layer in which the seeds can germinate. This method is particularly useful in the spot renovation of lawns or golf greens or fairways as the herbicidal effect of the composition of this invention can be greatly decreased or totally inactivated by contact with soil if the correct herbicide is chosen. Thus, seeds which are in the soil can germinate and grow without any apparent effects from the spraying of the unwanted plants prior to the time the seed actually germinates. The compositions of this invention provide a wide spectrum weed control and are also extremely useful as general herbicides as well as in controlling unwanted plants in orchards, tree farms and various crops. For example, by directing a spray of a synergistic mixture of this invention at the unwanted plant while essentially preventing such spray from contacting the leaves of trees, such unwanted plants are controlled while there is no apparent injury to the trees. In such directed spraying, the spray can fall on the woody portion of the fruit tree or other tree without any apparent effect. Thus, the directed spray method of control is useful with crops such as plantation crops, i.e. rubber, coffee, bananas, tea, etc. and in orchards such as citrus fruits, apples, peaches, pears, nuts, olive, in vine yards and in bramble crops an in nursery crops to control the undesired plants and in row crops such as cotton, soybeans, sugarcane and the like.

The syngergized compositions of this invention are also useful for the control of weeds between cropping seasons, for the renovation of stale seed beds and the like.

In applying the syngergistic compositions of this invention to the plants desired to control, it is desirable that the plant be emerged from the ground and even more desirable, that the plant be at least at the 2 leaf stage for maximum effect. The herbicide acts locally when the plants to be controlled have a portion of their growth above the ground or water, and the above-ground or above-water portion of the plant contacted with the herbicidal compositions of this invention at appropriate rates.

One can obtain limited selectivity in crops such as cotton, soybeans, sugar cane and the like, by directing a spray of a composition of this invention, at a selected concentration, on vegetation around the base of such plants with minimal spray contact with leafy portions of such crop plants. The direct spraying can be done with or without protective means to prevent contact of the spray with the leaves of such crop plants.

The phytotoxicant compositions, including concentrates which require dilution prior to application to the plants, of this invention contain at least one active ingredient and a synergistic adjuvant in dissolved form. The compositions are prepared by admixing the active herbicide and the syngergist with other adjuvants including diluents, extenders, carriers and conditioning agents to provide compositions in the form of finely-divided particulate solids, pellets, solutions, dispersions or emulsions. The active ingredients can be used with adjuvants such as a finely-divided solid, a liquid of organic origin, water, a wetting agent, a dispersing agent, an emulsifying agent or any suitable combination of these. From the viewpoint of economy and convenience, water is the preferred diluent.

The syngergistic phototoxicant compositions of this invention, particularly liquids and soluble powders, preferably contain as a conditioning agent one of more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. There are cases where anionic, cationic and non-ionic surface active agents can not be used with equal facility; i.e. are incompatible with a given herbicide or synergist. For example anionic detergents are incompatible with paraquat. Water-dispersible powder compositions can be made containing one or more active ingredients, an inert solid extender and one or more wetting and dispersing agents. The inert solid extenders are usually of mineral origin such as the natural clays, diatomaceous and earth and synthetic minerals derived from silica and the like. Examples of such extenders include kaolinites, attapulgite clay and synthetic magnesium silicate. They must not contain free copper, zinc or manganese ions or other metals that would complex chelating synergists. As some of the herbicides and synergists have low water solubility, aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform. Emulsifiable oils are usually solutions of active ingredient in water-immersible or partially water-immiscible solutions together with a surface active agent. Suitable solvents for the active ingredient of this invention include hydrocarbons and water-immiscible ethers, esters or ketones. The emulsifiable compositions generally contain from about 5 to 95 parts active ingredient, about 1 to 50 parts surface active agent and about 94 parts solvent, all parts being by weight based on the total weight of emulsifiable oil. Although compositions of this invention can also contain additives, for example fertilizers, phytotoxicants and plant growth regulating agents, pesticides and the like used as adjuvants or in combination with any of the above-described adjuvants, it is preferred to employ the compositions of this invention alone with sequential treatments with the other phytotoxicants, fertilizers and the like for maximum effect. Care must be taken that these additives do not contain ions that will be complexed with chelating agents, if the synergist is a chelator. For example the field could be sprayed with a composition of this invention before or after being treated with fertilizers, other phytotoxicants and the like. The compositions of this invention can also be admixed with other materials, e.g. fertilizers, other phytotoxicants, etc., and applied in a single application except when they interfere with the action of chelating synergists. When operating in accordance with the present invention, effective amounts of the synergistic compositions are applied to above ground portions of plants. The application of liquid and particulate solid herbicidal compositions to above ground portions of plants can be carried out by conventional methods, e.g. dusters, boom and hand sprayers and spray dusters. The compositions can also be applied from airplanes as a dust or spray because of their effectiveness at low dosages. The application of herbicidal compositions to aquatic plants is usually carried out by spraying the compositions on the aquatic plant in the area where control of the aquatic plants is desired. The application of effective amounts of the compound of this invention to the plant is essential and critical for the practice of the present invention. The exact amount of actual ingredients to be employed is dependent upon the response desired in the plant as well as other factors as the plant species and stage of development thereof, and the amount of rainfall, the amount of light as well as the specific mixture of herbicide and synergist employed. An effective amount for phytotoxic or herbicidal control is that amount necessary for overall or selective control, i.e. a phytotoxic or herbicidal amount. It is believed that one skilled in the art can readily determine from the teachings of this specification, including examples, the approximate application rates.

The compositions of the invention are highly effective as dessicating agents to aid crop harvesting and this use forms part of the invention.

We claim:

1. A herbicidal composition of enhanced activity comprising, in combination:
   a chemical or microbial herbicide which generates active oxygen species upon application to weeds; and
   a Cu or Zn chelating agent capable of at least partially inhibiting the activity of at least one plant enzyme of superoxide dismutase, ascorbate peroxidase and glutathione reductase,
   wherein said chelating agent is present in a quantity sufficient to at least partially inhibit the activity of the plant enzymes which take part in the pathway of detoxification of the active oxygen species generated by said herbicide, said amount being insufficient to cause death of the weed being treated when used alone, and
   wherein said herbicide is present in an amount sufficient to cause death of the weed being treated when administered in combination with said chelating agent.

2. A herbicidal composition in accordance with claim 1, wherein said chemical or microbial herbicide is selected from the group of classes of herbicides consisting of triazine, phenylurea, diphenyl-ether, uracil, bipyridillium and mycoherbicide classes.

3. A herbicidal composition in accordance with claim 2, wherein said chemical or microbial herbicide is selected from the group consisting of paraquat, oxyfluorfen, acifluorfen, diuron, bromacil and atrazine.

4. A herbicidal composition in accordance with claim 1, wherein said chelating agent is selected from the group consisting of diethyldithio-carbamate; α,α'-dipyridyl; ethylene diamine tetraacetic acid; tetraethylene pentaamine; ethylene triamine; salicyl aldoxime; p-hydroxy pyridine; oxime of 4-octyl-2-acetyl phenol and di-2-ethyl-hexyl phosphoric acid.

5. A herbicidal composition in accordance with claim 1, wherein said chemical or microbial herbicide is a bioherbicide or mycoherbicide which generates active oxygen species upon application to weeds.

6. A herbicidal composition in accordance with claim 2, where said chelating agent is selected from the group consisting of diethyldithio-carbamate; α,α'-dipyridyl; ethylene diamine tetraacetic acid; tetraethylene pentaamine; ethylene triamine; salicyl aldoxime; p-hydroxy pyridine; oxime of 4-octyl-2-acetyl phenol and, di-2-ethyl-hexyl phosphoric acid.

7. A herbicidal composition in accordance with claim 3, where said chelating agent is selected from the group consisting of diethyldithio-carbamate; α,α'-dipyridyl; ethylene diamine tetraacetic acid; tetraethylene pentaamine; ethylene triamine; salicyl aldoxime; p-hydroxy pyridine; oxime of 4-octyl-2-acetyl phenol and di-2-ethyl-hexyl phosphoric acid.

8. A process for effectively controlling plant growth and/or for eliminating certain plants and/or for desiccating plant parts prior to harvesting, comprising:
   applying to said plants an effective quantity of a chemical or microbial herbicide which generates active oxygen species upon application to plants; and
   applying to said plants a chelating agent for Cu or Zn capable of at least partially inhibiting the activity of plant enzymes which take part in the pathway of detoxification of active oxygen species in plants, said application being in a manner such that both said herbicide and said enzyme inhibitor are present on the plant at the same time,
   wherein said chelating agent is present in a quantity sufficient to at least partially inhibit the activity of plant enzymes which take part in the pathway of detoxification of the active oxygen species generated by said herbicide, said amount being insufficient to cause death of the plant being treated when used alone, and
   wherein said herbicide is present in an amount sufficient to cause the control, elimination or desiccation of said plant being treated when present on the plant in combination with said chelating agent.

9. A process in accordance with claim 8, wherein the quantities of said herbicide and said chelating agent are selected in such a manner as to result in a selective herbicidal action on undesired weeds, substantially not affecting desired crop plants.

10. A process in accordance with claim 8, wherein said chemical or microbial herbicide is selected from a group of classes of herbicides consisting of triazine, phenylurea, diphenyl-ether, uracil, bipyridillium and mycoherbicide classes.

11. A process in accordance with claim 8, wherein said chemical or microbial herbicide is selected from the group consisting of paraquat, oxyfluorfen, acifluorfen, diuron, bromacil and atrazine.

12. A process in accordance with claim 8, wherein said chelating agent is selected from the group consisting of diethyldithio-carbamate; α,α'-dipyridyl; ethylene diamine tetraacetic acid; tetraethylene pentaamine; ethylene triamine; salicyl aldoxime; p-hydroxy pyridine; oxime of 4-octyl-2-acetyl phenol and di-2-ethyl-hexyl phosphoric acid.

13. A process in accordance with claim 8, wherein said herbicide and said chelating agent are applied to the leaves of said plants.

* * * * *

UNITED STATES PATENT AND TRADEMARK OFFICE
CERTIFICATE OF CORRECTION

PATENT NO. : 5,219,825
DATED : June 15, 1993
INVENTOR(S) : Gressel et al

It is certified that error appears in the above-indentified patent and that said Letters Patent is hereby corrected as shown below:

Column 1, line 37, change "Digitaria" (not italicized) to --*Digitaria*-- (italicized).

Column 1, line 50, after "Scheme 1:" insert --The superoxide dismutating system in plants.--

Columns 1-2, within Scheme 1, change the spelling of "Giuiathione" at all three occurrences to --Glutathione--.

Column 1, line 56, delete "The superoxide dismutating system in plants."

Column 1, line 59, change the spelling of "Fover" to --Foyer--.

Column 1, line 62, replace "Press" with --Publ.--.

Column 2, line 7, after "paraquat" delete the period ".".

Column 2, line 36, replace "Press" with --Publ.--.

Column 3, line 54, replace "class" with --classes--.

Column 5, line 39, replace "ganella" with --ganellar--.

Column 7, line 10, replace "superoxides" with --superoxide--.

Column 7, line 33, replace "chloroplast" with --chloroplasts--.

Column 7, line 40, replace "chloroplants" with --chloroplasts--.

UNITED STATES PATENT AND TRADEMARK OFFICE
CERTIFICATE OF CORRECTION

PATENT NO. : 5,219,825
DATED : June 15, 1993
INVENTOR(S) : Gressel et al

It is certified that error appears in the above-indentified patent and that said Letters Patent is hereby corrected as shown below:

Column 7, line 52, replace "three" with --there--.

Column 8, line 18, third column, replace "oxident" with --oxidant--.

Column 8, line 62, replace "and" with --as--.

Column 9, line 9, replace "was" with --were--.

Column 9, line 59, fifth column, replace "9" with --79--.

Column 11, line 24, replace "herbicides" with --herbicide--.

Column 12, line 39, after "only" insert a comma --,--.

Column 13, line 30, replace "direct" with --directed--.

Column 13, line 59, replace "can not" with --cannot--.

Signed and Sealed this

Twenty-fourth Day of January, 1995

Attest:

BRUCE LEHMAN

Attesting Officer

Commissioner of Patents and Trademarks